US00PP30337P2

(12) United States Plant Patent
van den Top

(10) Patent No.: US PP30,337 P2
(45) Date of Patent: Apr. 2, 2019

(54) ***HOSTA* PLANT NAMED 'B201'**

(50) Latin Name: *Hosta hybrida*
Varietal Denomination: B201

(71) Applicant: Hendrik Jan van den Top, Barneveld (NL)

(72) Inventor: Hendrik Jan van den Top, Barneveld (NL)

( * ) Notice: Subject to any disclaimer, the term of this patent is extended or adjusted under 35 U.S.C. 154(b) by 0 days.

(21) Appl. No.: 15/732,442

(22) Filed: Nov. 13, 2017

(51) Int. Cl.
*A01H 5/02* (2018.01)

(52) U.S. Cl.
USPC ..... Plt./353

(58) Field of Classification Search
USPC ..... Plt./263.1, 353
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hosta* named 'B201' that is characterized by its leaf petioles and flower stems that are dark red in color, its foliage that is glossy green in color with broad margins that emerge yellow and turn to creamy white in color, its leaves that are thick and strong, its vigorous growth habit and its high resistance to slugs.

3 Drawing Sheets

Botanical classification: *Hosta hybrida.*
Cultivar designation: 'B201'.

BACKGROUND OF THE INVENTION

The present invention relates to a new and distinct cultivar of *Hosta*, botanically of hybrid origin and known as a *Hosta* 'B201' and is hereinafter referred to by its cultivar name 'B201'.

The new cultivar was discovered by the Inventor in June of 2011 as a naturally-occuring chimeral mutation of an unnamed *Hosta* plant from the Inventor's breeding program that was growing in a container outdoors in Barneveld, The Netherlands.

Asexual propagation of the new cultivar was first accomplished by division by the Inventor in Barneveld, The Netherlands in 2013. Asexual propagation of the new cultivar by division and tissue culture using meristematic tissue has shown that the unique features are stable and reproduced true to type in successive generations.

SUMMARY OF THE INVENTION

The following traits have been repeatedly observed and represent the characteristics of the new cultivar. These attributes in combination distinguish 'B201' as a new and unique cultivar of *Hosta.*

1. 'B201' exhibits leaf petioles and flower stems that are dark red in color.
2. 'B201' exhibits foliage that is glossy green in color with broad margins that emerge yellow and turn creamy white in color.
3. 'B201' exhibits leaves that are thick and strong.
4. 'B201' exhibits a vigorous growth habit.
5. 'B201' exhibits high resistance to slugs.

The parent plant differs from 'B201' in having much thinner margins and leaves that are thinner with less substance. 'B201' can be most closely compared to the *Hosta* cultivar 'Secret Treasure' (U.S. Plant Pat. No. 22,789).

'Secret Treasure' is similar to 'B201' in leaf vareigation pattern and in having red stems. 'Secret Treasure' differs from 'B201' in having thinner leaves with less substance, thinner leaf margins, and a taller plant height.

BRIEF DESCRIPTION OF THE DRAWINGS

The accompanying colored photographs illustrate the overall appearance and distinct characteristics of the new *Hosta*. The photographs were taken of 2 year-old plants as grown outdoors in a 27-cm container in Barneveld, The Netherlands.

Figure 1:
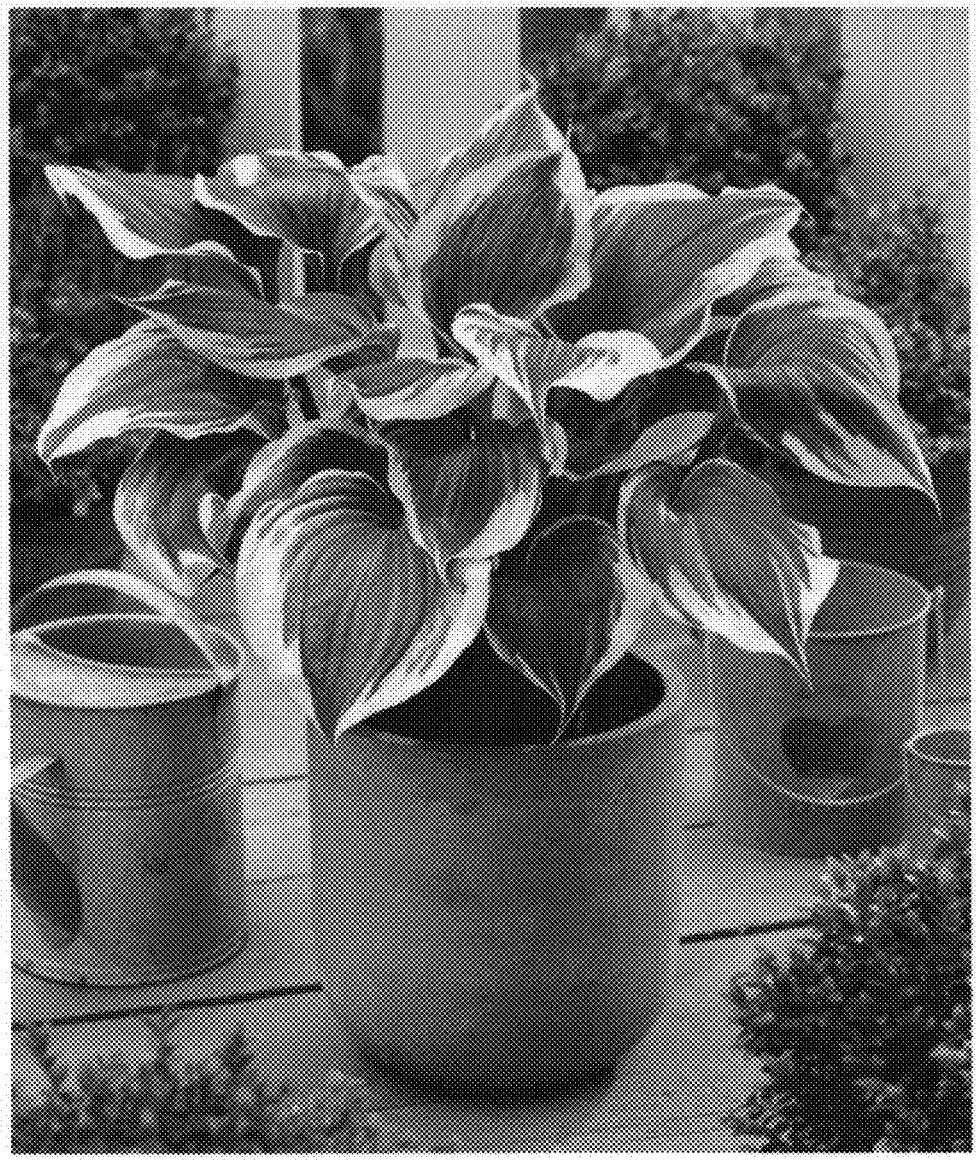
FIG. 1 provides an overall view of the plant of 'B201'.
Figure 2:
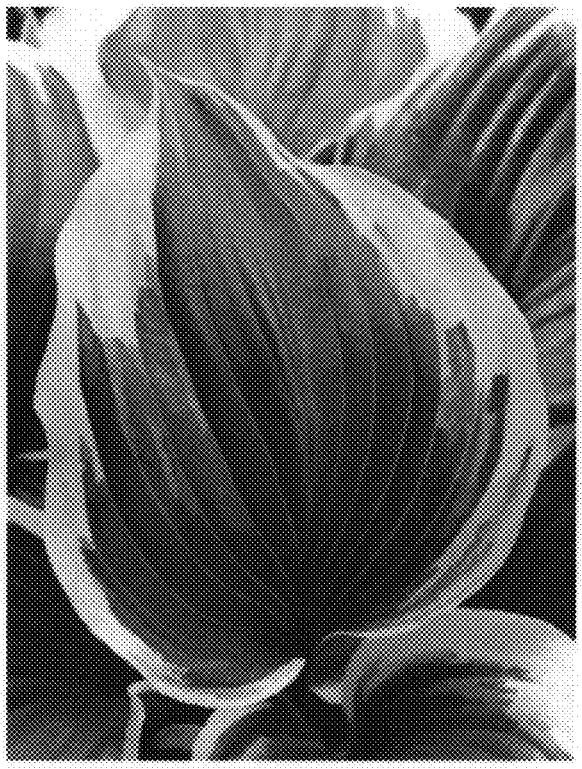

The photograph in FIG. 2 provides a close-up view of a leaf of 'B201'.

Figure 3:
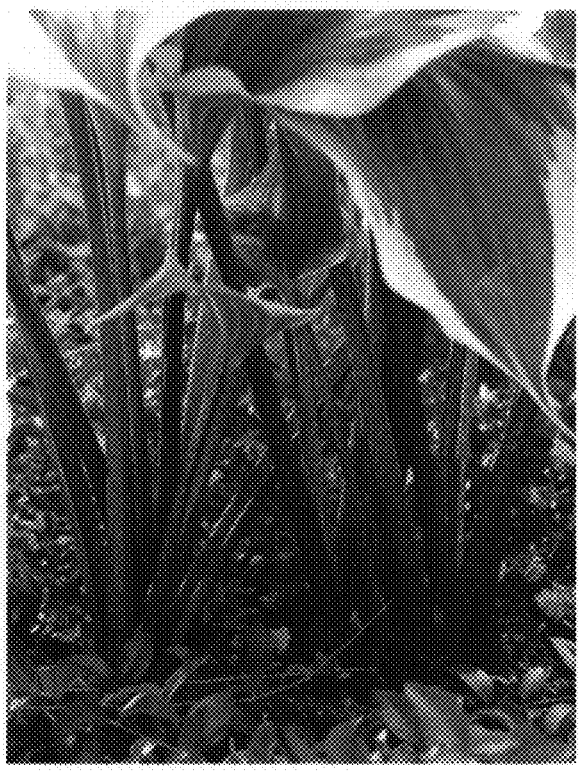

FIG. 3 provides a close-up view of the leaf petioles of 'B201'.

Figure 4:
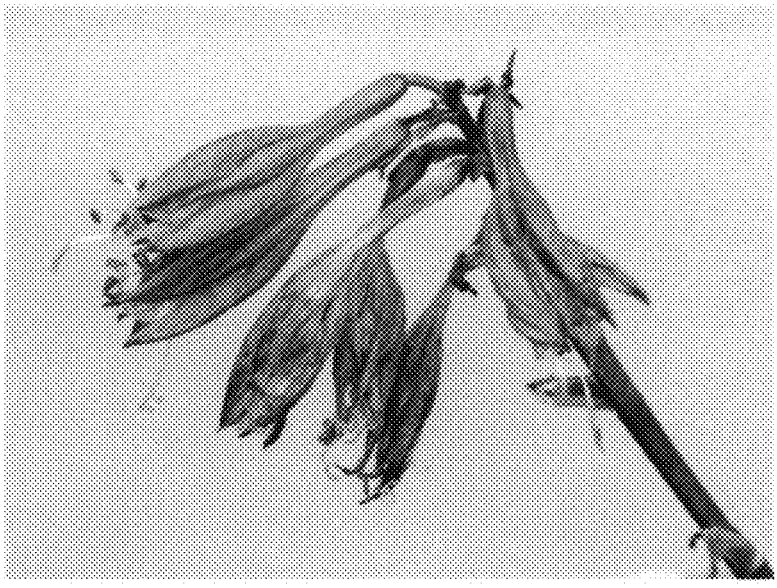

FIG. 4 provides a close-up view of an inflorescence of 'B201'.

The colors in the photographs are as close as possible with the photographic and printing technology utilized and the color values cited in the Detailed Botanical Description accurately describe the colors of the new *Hosta.*

DETAILED BOTANICAL DESCRIPTION OF THE PLANT

The following is a detailed description of 2 year-old plants as grown outdoors in a 17-cm container in Barneveld, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—In September into October in The Netherlands.

*Plant type*.—Herbaceous perennial.

*Plant habit*.—Broad spreading to upright, compact.

*Height and spread*.—An average of 33 cm in height (to top of foliage), 38.4 cm in height (to top of inflorescence) and 40 cm in width as a 2 year-old plant.

*Cold hardiness*.—At least in U.S.D.A. Zones 4 to 10.

*Diseases and pests*.—No susceptibility to resistance to diseases has been observed, high resistance to slugs has been observed.

*Root description*.—Freely branched, fleshy, 162D in color.

*Root development*.—About 20 weeks to produce a fully rooted plant in a 13-cm container.

*Propagation*.—Tissue culture preferred, division is also possible.

*Growth rate*.—Vigorous.

Foliage description:

*Leaf shape*.—Broadly ovate.

*Leaf division*.—Simple.

*Leaf base*.—Broad attenuate.

*Leaf apex*.—Apiculate.

*Leaf venation*.—Camptodrome pattern, upper surface color; 144B, lower surface color; 148D, main vein dotted and blotched towards the base, 187C.

*Leaf margins*.—Entire, coarsely undulate.

*Leaf attachment*.—Petiolate.

*Leaf aspect*.—Slightly irregular convexed.

*Leaf arrangement*.—Alternate, in basal rosettes.

*Leaf surface*.—Upper and lower surface is glabrous, smooth, moderately glossy and leathery, non-rugose.

*Leaf orientation*.—Held nearly upright to slightly outward on upright petioles.

*Leaf color*.—Young upper surface; between 137B and 144A, irregularity and broadly margined 145A, 145B and 150B, young leaf lower surface; 143A, irregularity and broadly margined 10B to 10C and 145B, mature upper surface; 137B, N138B and 191B, irregularity and broadly margined 147D, 10C and 10D and 160C, mature lower surface; 144B, 146A and 146B and 143B, irregularity broadly margined 150D.

*Leaf size*.—Average of 20.8 cm in length and 13.9 cm in width.

*Leaf quantity*.—Average of 4 per basal rosette.

*Petioles*.—Average of 27.1 cm in length, average of 8 mm in diameter, both surfaces are glabrous and smooth, u-shaped, strong, color upper surface; 143C and very heavily blotched N186C, color lower surface; 144B and very heavily blotched 187B.

Flower description:

*Inflorescence type*.—Terminal racemes of single bell-shaped flowers.

*Inflorescence size*.—14.6 cm in height, 6.1 cm in width.

*Lastingness of inflorescence*.—About 4 weeks from first opening bloom to fading of last opening bloom, individual blooms last up to 5 days, self cleaning.

*Flower type*.—Campanulate, single.

*Flower/inflorescence number*.—Average of 10 inflorescences per plant, 11 flowers per inflorescence.

*Flower fragrance*.—None.

*Flower aspect*.—Drooping.

*Flower buds*.—Average of 3 cm in length, 1.4 cm in diameter, spathulate in shape, smooth, glabrous and moderately glossy surface, color; N77D.

*Flower size*.—Average of 2.2 cm in depth, 2.3 cm in diameter.

*Peduncles*.—An average of 31.3 cm in length, 4 mm in diameter, held in an average angle of 25°, strong, smooth and glabrous surface, 184A in color.

*Pedicels*.—An average of 7 mm in length, 1.5 mm in diameter, held in an average angle of 50°, moderately strong, smooth and glabrous surface, 79D in color.

*Calyx*.—Campanulate in shape, 4.7 cm in length, 2.2 cm in diameter.

*Tepals*.—6, rotate, fused into campanulate shape, 57% of the tepals are fused, glabrous, slightly glossy and dull surfaces, entire margins, acute apex, 4.7 cm in length, outer tepal 6 mm in width, color; when opening and fully open upper surface N77C, when opening and fully open lower surface N77D, upper and lower surface fading to N92B, flower throat and vein color N77C, flower tube and vein color N77B.

*Floral bracts*.—1 at the base of each pedicel, ovate in shape, apiculate apex, truncate base, both surfaces are smooth and glabrous, average of 1.6 cm in length and 4 mm in width, color of both surfaces a color between N77C and 79D.

Reproductive organs:

*Gynoecium*.—Pistil; 1, 4.9 cm in length, style; 4.8 cm in length, 157D, stigma; crested in shape, 1 mm in length and diameter, 160D in color.

*Androecium*.—Stamens; 6, filament; curled, NN155B in color, anthers; 2.5 mm in length, 1.5 mm in width, N187A in color, pollen is abundant and 14A in color.

*Fruit/seed*.—Production of seed capsules was not observed to date.

It is claimed:

1. A new and distinct cultivar of *Hosta* plant named 'B201' as herein illustrated and described.

* * * * *